(12) United States Patent
Han et al.

(10) Patent No.: US 12,257,287 B2
(45) Date of Patent: Mar. 25, 2025

(54) GLUCAGON-DERIVED PEPTIDE AND USE THEREOF

(71) Applicant: Tianjin Institute of Pharmaceutical Research Co., Ltd., Tianjin (CN)

(72) Inventors: Yingmei Han, Tianjin (CN); Wei Liu, Tianjin (CN); Bingni Liu, Tianjin (CN); Weiling Kong, Tianjin (CN); Naxia Zhao, Tianjin (CN); Guangping Xia, Tianjin (CN); Qian Shang, Tianjin (CN); Xiaohua Kong, Tianjin (CN); Jing Jin, Tianjin (CN); Yuquan Li, Tianjin (CN); Xuyuan Liu, Tianjin (CN)

(73) Assignee: Tianjin Institute of Pharmaceutical Research Co., Ltd., Tianjin (CN)

( * ) Notice: Subject to any disclaimer, the term of this patent is extended or adjusted under 35 U.S.C. 154(b) by 118 days.

(21) Appl. No.: 17/292,922

(22) PCT Filed: Nov. 12, 2019

(86) PCT No.: PCT/CN2019/117715
§ 371 (c)(1),
(2) Date: May 11, 2021

(87) PCT Pub. No.: WO2020/103729
PCT Pub. Date: May 28, 2020

(65) Prior Publication Data
US 2024/0252592 A1    Aug. 1, 2024

(30) Foreign Application Priority Data

Nov. 12, 2018 (CN) .......................... 201811338218.2

(51) Int. Cl.
| A61K 38/26 | (2006.01) |
| A61P 3/04 | (2006.01) |
| A61P 3/10 | (2006.01) |

(52) U.S. Cl.
CPC ................ *A61K 38/26* (2013.01); *A61P 3/04* (2018.01); *A61P 3/10* (2018.01)

(58) Field of Classification Search
CPC ............... A61K 38/26; A61P 3/04; A61P 3/10
See application file for complete search history.

(56) References Cited

U.S. PATENT DOCUMENTS

| 2016/0368960 A1 | 12/2016 | Mezo et al. |
| 2019/0117737 A1 | 4/2019 | Jiang et al. |
| 2023/0174608 A1* | 6/2023 | Han .......................... A61P 3/10 514/7.2 |

FOREIGN PATENT DOCUMENTS

| CA | 3084005 C | * 12/2018 | ............. A61K 38/26 |
| CN | 1311687 A | 9/2001 | |
| CN | 102123723 A | 7/2011 | |
| CN | 102459325 A | 5/2012 | |
| CN | 104822699 A | 8/2015 | |
| CN | 106046145 A | 10/2016 | |
| CN | 107735100 A | 2/2018 | |
| CN | 108135981 A | 6/2018 | |
| CN | 108341879 A | 7/2018 | |
| IN | 104583232 A | 4/2015 | |
| WO | 99/64061 A1 | 12/1999 | |
| WO | 2009/155258 A2 | 12/2009 | |
| WO | 2010/148089 A1 | 12/2010 | |
| WO | 2013/192129 A1 | 12/2013 | |
| WO | 2014/091316 A2 | 10/2014 | |
| WO | 2016/209707 A1 | 12/2016 | |
| WO | 2017/074714 A1 | 5/2017 | |

OTHER PUBLICATIONS

Evers, A., et al., "Design of Novel Exendin-Based Dual Glucagon-Like Peptide 1 (GLP-1)/Glucagon Receptor Agonists," Journal of Medicinal Chemistry 60(10):4293-4303, May 2017.
Evers, A., et al., "Dual Glucagon-Like Peptide 1 (GLP-1)/Glucagon Receptor Agonists Specifically Optimized for Multidose Formulations," Journal of Medicinal Chemistry 61(13):5580-5593, Jul. 2018.
Extended European Search Report mailed Aug. 2, 2022, issued in EP Application No. 19886965.3, filed Nov. 12, 2019, 11 pages.
Written Opinion mailed Feb. 3, 2020, issued in International Application No. PCT/CN2019/117715, filed Nov. 12, 2019, 9 pages.
International Preliminary Report on Patentability mailed May 11, 2021, issued in International Application No. PCT/CN2019/117715, filed Nov. 12, 2019, 5 pages.
International Search Report mailed Feb. 3, 2020, issued in International Application No. PCT/CN2019/117715, filed Nov. 12, 2019, 20 pages.

* cited by examiner

*Primary Examiner* — Marcela M Cordero Garcia
(74) *Attorney, Agent, or Firm* — Christensen O'Connor Johnson Kindness, PLLC

(57) ABSTRACT

Provided are a polypeptide derivative, modified derivative or salt thereof, and use of the polypeptide derivative, modified derivative or salt thereof, wherein the polypeptide derivative, modified derivative or salt thereof comprises a polypeptide having the sequence of following general formula I, general formula I:

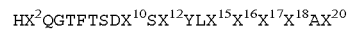

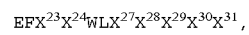

wherein the definitions of $X^2$, $X^{10}$, $X^{12}$, $X^{15}$, $X^{16}$, $X^{17}$, $X^{18}$, $X^{20}$, $X^{23}$, $X^{24}$, $X^{27}$, $X^{28}$, $X^{29}$, $X^{30}$ and $X^{31}$ are consistent with the definitions in the claims and the description. The polypeptide derivative provided by the invention has a dual agonistic effect on GC/GLP-1 receptors, so that a synergistic effect on energy metabolism is generated, which can effectively reduce blood glucose while reducing body weight and improving the body fat level, and the efficacy is better than that of a single GLP-1 receptor agonist.

20 Claims, 1 Drawing Sheet
Specification includes a Sequence Listing.

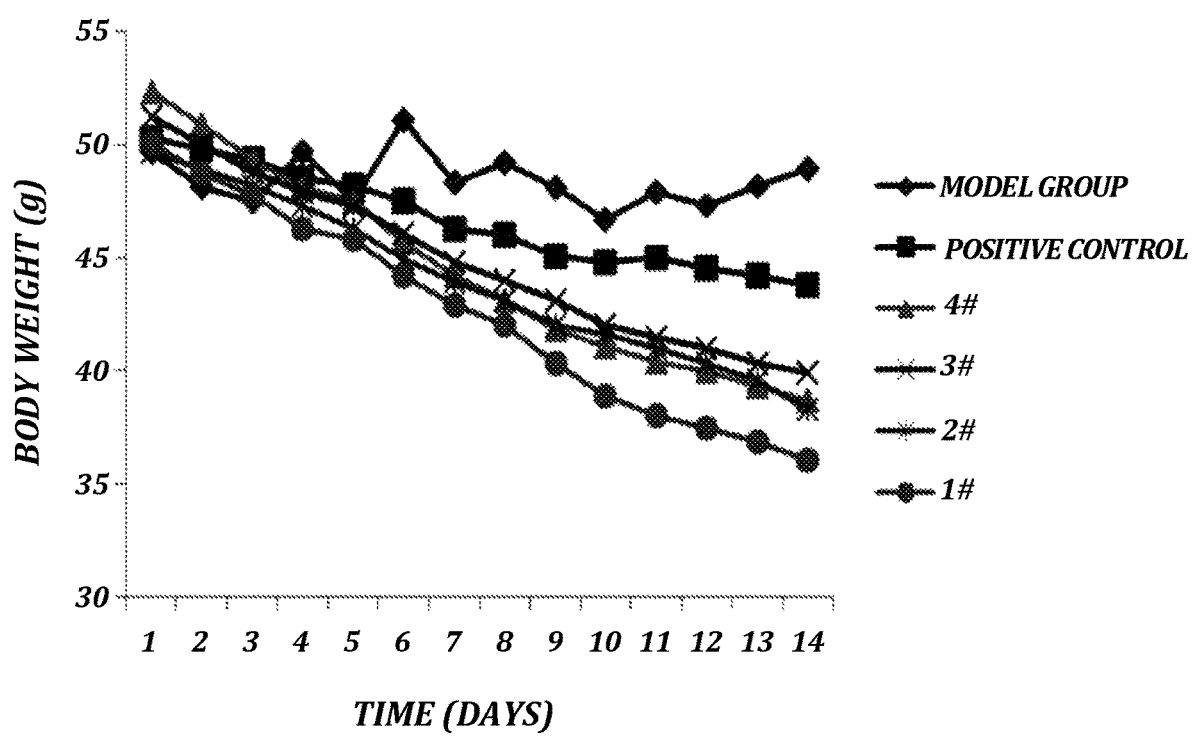

```
                     SEQUENCE LISTING

<160> NUMBER OF SEQ ID NOS: 43

<210> SEQ ID NO 1
<211> LENGTH: 30
<212> TYPE: PRT
<213> ORGANISM: Artificial Sequence
<220> FEATURE:
<223> OTHER INFORMATION: Synthetic

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: Synthetic

<400> SEQUENCE: 2

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 3
<211> LENGTH: 37
<212> TYPE: PRT
<213> ORGANISM: Artificial Sequence
<220> FEATURE:
<223> OTHER INFORMATION: Synthetic

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30
```

Arg Asn Asn Ile Ala
        35

<210> SEQ ID NO 4
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: Lysine is attached to a fatty side chain
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 4

His Xaa Gln Gly Thr Phe Thr Ser Asp Lys Ser Lys Tyr Leu Xaa Glu
1               5                   10                  15

Arg Ala Ala Lys Glu Phe Ile Xaa Trp Leu Glu Ala Gly Gly Pro Ser
            20                  25                  30

Ser Gly

<210> SEQ ID NO 5
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: Lysine is attached to a fatty side chain
<220> FEATURE:
<221> NAME/KEY: MUTAGEN
<222> LOCATION: (24)..(24)
<223> OTHER INFORMATION: Xaa is Ala or Glu

<400> SEQUENCE: 5

His Xaa Gln Gly Thr Phe Thr Ser Asp Tyr Ser Lys Tyr Leu Xaa Glu
1               5                   10                  15

Arg Ala Ala Lys Glu Phe Val Xaa Trp Leu Glu Ala Gly Gly Pro Ser
            20                  25                  30

Ser Gly

<210> SEQ ID NO 6
<211> LENGTH: 34
<212> TYPE: PRT
<213> ORGANISM: Artificial Sequence
<220> FEATURE:
<223> OTHER INFORMATION: Synthetic
<220> FEATURE:

```
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: Lysine is attached to a fatty side chain
<220> FEATURE:
<221> NAME/KEY: MUTAGEN
<222> LOCATION: (24)..(24)
<223> OTHER INFORMATION: Xaa is Ala or Glu

<400> SEQUENCE: 6

His Xaa Gln Gly Thr Phe Thr Ser Asp Tyr Ser Lys Tyr Leu Xaa Glu
1               5                   10                  15

Arg Ala Ala Lys Glu Phe Val Xaa Trp Leu Glu Ala Gly Gly Pro Ser
            20                  25                  30

Ser Gly

<210> SEQ ID NO 7
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: Lysine is attached to a fatty side chain
<220> FEATURE:
<221> NAME/KEY: MUTAGEN
<222> LOCATION: (24)..(24)
<223> OTHER INFORMATION: Xaa is Ala or Glu

<400> SEQUENCE: 7

His Xaa Gln Gly Thr Phe Thr Ser Asp Tyr Ser Lys Tyr Leu Xaa Glu
1               5                   10                  15

Arg Lys Ala Lys Glu Phe Val Xaa Trp Leu Glu Ala Gly Gly Pro Ser
            20                  25                  30

Ser Gly

<210> SEQ ID NO 8
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: Lysine is attached to a fatty side chain
```

```
<220> FEATURE:
<221> NAME/KEY: MUTAGEN
<222> LOCATION: (24)..(24)
<223> OTHER INFORMATION: Xaa is Ala or Glu

<400> SEQUENCE: 8

His Xaa Gln Gly Thr Phe Thr Ser Asp Tyr Ser Lys Tyr Leu Xaa Glu
1               5                   10                  15

Arg Lys Ala Lys Glu Phe Ile Xaa Trp Leu Glu Ala Gly Gly Pro Ser
            20                  25                  30

Ser Gly

<210> SEQ ID NO 9
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: Lysine is attached to a fatty side chain
<220> FEATURE:
<221> NAME/KEY: MUTAGEN
<222> LOCATION: (24)..(24)
<223> OTHER INFORMATION: Xaa is Ala or Glu

<400> SEQUENCE: 9

His Xaa Gln Gly Thr Phe Thr Ser Asp Tyr Ser Lys Tyr Leu Xaa Glu
1               5                   10                  15

Lys Arg Ala Lys Glu Phe Ile Xaa Trp Leu Glu Ala Gly Gly Pro Ser
            20                  25                  30

Ser Gly

<210> SEQ ID NO 10
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: Lysine is attached to a fatty side chain
<220> FEATURE:
<221> NAME/KEY: MUTAGEN
<222> LOCATION: (24)..(24)
<223> OTHER INFORMATION: Xaa is Ala or Glu

<400> SEQUENCE: 10

His Xaa Gln Gly Thr Phe Thr Ser Asp Tyr Ser Lys Tyr Leu Xaa Glu
1               5                   10                  15

Lys Arg Ala Lys Glu Phe Val Xaa Trp Leu Glu Ala Gly Gly Pro Ser
```

Ser Gly

<210> SEQ ID NO 11
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: Lysine amino group is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 11

His Xaa Gln Gly Thr Phe Thr Ser Asp Lys Ser Lys Tyr Leu Xaa Glu
1               5                   10                  15

Arg Ala Ala Lys Glu Phe Val Xaa Trp Leu Glu Ala Gly Gly Pro Ser
            20                  25                  30

Ser Gly

<210> SEQ ID NO 12
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 12

His Xaa Gln Gly Thr Phe Thr Ser Asp Lys Ser Lys Tyr Leu Xaa Glu
1               5                   10                  15

Arg Lys Ala Lys Glu Phe Val Xaa Trp Leu Glu Ala Gly Gly Pro Ser
            20                  25                  30

Ser Gly

<210> SEQ ID NO 13
<211> LENGTH: 34
<212> TYPE: PRT
<213> ORGANISM: Artificial Sequence
<220> FEATURE:
<223> OTHER INFORMATION: Synthetic

```
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: Lysine amino group is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 13

His Xaa Gln Gly Thr Phe Thr Ser Asp Lys Ser Lys Tyr Leu Xaa Glu
1               5                   10                  15

Arg Lys Ala Lys Glu Phe Ile Xaa Trp Leu Glu Ala Gly Gly Pro Ser
            20                  25                  30

Ser Gly

<210> SEQ ID NO 14
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: Lysine amino group is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 14

His Xaa Gln Gly Thr Phe Thr Ser Asp Lys Ser Lys Tyr Leu Xaa Glu
1               5                   10                  15

Lys Arg Ala Lys Glu Phe Ile Xaa Trp Leu Glu Ala Gly Gly Pro Ser
            20                  25                  30

Ser Gly

<210> SEQ ID NO 15
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: amino group of Lysine is modified
<220> FEATURE:
<221> NAME/KEY: MUTAGEN
<222> LOCATION: (15)..(15)
```

```
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 15

His Xaa Gln Gly Thr Phe Thr Ser Asp Lys Ser Lys Tyr Leu Xaa Glu
1               5                   10                  15

Lys Arg Ala Lys Glu Phe Val Xaa Trp Leu Glu Ala Gly Gly Pro Ser
            20                  25                  30

Ser Gly

<210> SEQ ID NO 16
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: amino group of Lysine is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 16

His Xaa Gln Gly Thr Phe Thr Ser Asp Lys Ser Lys Tyr Leu Xaa Glu
1               5                   10                  15

Arg Ala Ala Lys Glu Phe Ile Xaa Trp Leu Gly Gly Pro Ser Ser
            20                  25                  30

Gly

<210> SEQ ID NO 17
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: amino group of Lysine is modified
<220> FEATURE:
<221> NAME/KEY: MUTAGEN
<222> LOCATION: (24)..(24)
<223> OTHER INFORMATION: Xaa is Ala or Glu

<400> SEQUENCE: 17

His Xaa Gln Gly Thr Phe Thr Ser Asp Tyr Ser Lys Tyr Leu Xaa Glu
1               5                   10                  15
```

Arg Ala Ala Lys Glu Phe Ile Xaa Trp Leu Glu Gly Gly Pro Ser Ser
            20                  25                  30

Gly

<210> SEQ ID NO 18
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: amino group of Lysine is modified
<220> FEATURE:
<221> NAME/KEY: MUTAGEN
<222> LOCATION: (24)..(24)
<223> OTHER INFORMATION: Xaa is Ala or Glu

<400> SEQUENCE: 18

His Xaa Gln Gly Thr Phe Thr Ser Asp Tyr Ser Lys Tyr Leu Xaa Glu
1               5                   10                  15

Arg Ala Ala Lys Glu Phe Val Xaa Trp Leu Glu Gly Gly Pro Ser Ser
            20                  25                  30

Gly

<210> SEQ ID NO 19
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: amino group of Lysine is modified
<220> FEATURE:
<221> NAME/KEY: BINDING
<222> LOCATION: (24)..(24)
<223> OTHER INFORMATION: Xaa is Ala or Glu

<400> SEQUENCE: 19

His Xaa Gln Gly Thr Phe Thr Ser Asp Tyr Ser Lys Tyr Leu Xaa Glu
1               5                   10                  15

Arg Lys Ala Lys Glu Phe Val Xaa Trp Leu Glu Gly Gly Pro Ser Ser
            20                  25                  30

Gly

<210> SEQ ID NO 20
<211> LENGTH: 33
<212> TYPE: PRT
<213> ORGANISM: Artificial Sequence
<220> FEATURE:

```
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: amino group of Lysine is modified
<220> FEATURE:
<221> NAME/KEY: MUTAGEN
<222> LOCATION: (24)..(24)
<223> OTHER INFORMATION: Xaa is Ala or Glu

<400> SEQUENCE: 20

His Xaa Gln Gly Thr Phe Thr Ser Asp Tyr Ser Lys Tyr Leu Xaa Glu
 1               5                  10                  15

Arg Lys Ala Lys Glu Phe Ile Xaa Trp Leu Glu Gly Gly Pro Ser Ser
            20                  25                  30

Gly

<210> SEQ ID NO 21
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
<222> LOCATION: (20)..(20)
<223> OTHER INFORMATION: amino group of Lysine is modified
<220> FEATURE:
<221> NAME/KEY: MUTAGEN
<222> LOCATION: (24)..(24)
<223> OTHER INFORMATION: Xaa is Ala or Glu

<400> SEQUENCE: 21

His Xaa Gln Gly Thr Phe Thr Ser Asp Tyr Ser Lys Tyr Leu Xaa Glu
 1               5                  10                  15

Lys Arg Ala Lys Glu Phe Ile Xaa Trp Leu Glu Gly Gly Pro Ser Ser
            20                  25                  30

Gly

<210> SEQ ID NO 22
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: BINDING
```

```
<222> LOCATION: (20)..(20)
<223> OTHER INFORMATION: amino group of Lysine is modified
<220> FEATURE:
<221> NAME/KEY: MUTAGEN
<222> LOCATION: (24)..(24)
<223> OTHER INFORMATION: Xaa is Ala or Glu

<400> SEQUENCE: 22

His Xaa Gln Gly Thr Phe Thr Ser Asp Tyr Ser Lys Tyr Leu Xaa Glu
1               5                   10                  15

Lys Arg Ala Lys Glu Phe Val Xaa Trp Leu Glu Gly Gly Pro Ser Ser
            20                  25                  30

Gly

<210> SEQ ID NO 23
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: amino group of Lysine is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 23

His Xaa Gln Gly Thr Phe Thr Ser Asp Lys Ser Lys Tyr Leu Xaa Glu
1               5                   10                  15

Arg Ala Ala Lys Glu Phe Val Xaa Trp Leu Glu Gly Gly Pro Ser Ser
            20                  25                  30

Gly

<210> SEQ ID NO 24
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: amino group of Lysine is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 24

His Xaa Gln Gly Thr Phe Thr Ser Asp Lys Ser Lys Tyr Leu Xaa Glu
1               5                   10                  15
```

Arg Lys Ala Lys Glu Phe Val Xaa Trp Leu Glu Gly Gly Pro Ser Ser
            20                  25                  30

Gly

<210> SEQ ID NO 25
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: amino group of Lysine is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 25

His Xaa Gln Gly Thr Phe Thr Ser Asp Lys Ser Lys Tyr Leu Xaa Glu
1               5                   10                  15

Arg Lys Ala Lys Glu Phe Ile Xaa Trp Leu Glu Gly Gly Pro Ser Ser
            20                  25                  30

Gly

<210> SEQ ID NO 26
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: amino group of Lysine is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 26

His Xaa Gln Gly Thr Phe Thr Ser Asp Lys Ser Lys Tyr Leu Xaa Glu
1               5                   10                  15

Lys Arg Ala Lys Glu Phe Ile Xaa Trp Leu Glu Gly Gly Pro Ser Ser
            20                  25                  30

Gly

<210> SEQ ID NO 27
<211> LENGTH: 33
<212> TYPE: PRT
<213> ORGANISM: Artificial Sequence

```
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Ser or Aib
<220> FEATURE:
<221> NAME/KEY: BINDING
<222> LOCATION: (10)..(10)
<223> OTHER INFORMATION: amino group of Lysine is modified
<220> FEATURE:
<221> NAME/KEY: MUTAGEN
<222> LOCATION: (15)..(15)
<223> OTHER INFORMATION: Xaa is Asp or Glu
<220> FEATURE:
<221> NAME/KEY: MUTAGEN
<222> LOCATION: (24)..(24)
<223> OTHER INFORMATION: Xaa is Ala or Glu

<400> SEQUENCE: 27

His Xaa Gln Gly Thr Phe Thr Ser Asp Lys Ser Lys Tyr Leu Xaa Glu
1               5                   10                  15

Lys Arg Ala Lys Glu Phe Val Xaa Trp Leu Glu Gly Gly Pro Ser Ser
            20                  25                  30

Gly

<210> SEQ ID NO 28
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Aib
<220> FEATURE:
<221> NAME/KEY: BINDING
<222> LOCATION: (17)..(17)
<223> OTHER INFORMATION: amino group of Lysine is modified

<400> SEQUENCE: 28

His Xaa Gln Gly Thr Phe Thr Ser Asp Tyr Ser Lys Tyr Leu Glu Glu
1               5                   10                  15

Lys Arg Ala Arg Glu Phe Val Ala Trp Leu Leu Glu Gly Gly Pro Ser
            20                  25                  30

Ser Gly

<210> SEQ ID NO 29
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Aib
<220> FEATURE:
<221> NAME/KEY: BINDING
<222> LOCATION: (10)..(10)
<223> OTHER INFORMATION: amino group of Lysine is modified

<400> SEQUENCE: 29

His Xaa Gln Gly Thr Phe Thr Ser Asp Lys Ser Lys Tyr Leu Glu Glu
1               5                   10                  15

Arg Ala Ala Lys Glu Phe Val Ala Trp Leu Lys Glu Gly Gly Pro Ser
            20                  25                  30
```

-continued

Ser Gly

<210> SEQ ID NO 30
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Aib
<220> FEATURE:
<221> NAME/KEY: BINDING
<222> LOCATION: (10)..(10)
<223> OTHER INFORMATION: amino group of Lysine is modified

<400> SEQUENCE: 30

His Xaa Gln Gly Thr Phe Thr Ser Asp Lys Ser Lys Tyr Leu Glu Glu
1               5                   10                  15

Arg Ala Ala Lys Glu Phe Val Glu Trp Leu Val Lys Gly Glu Gly Gly
            20                  25                  30

Pro Ser Ser Gly
        35

<210> SEQ ID NO 31
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Aib
<220> FEATURE:
<221> NAME/KEY: BINDING
<222> LOCATION: (10)..(10)
<223> OTHER INFORMATION: amino group of Lysine is modified

<400> SEQUENCE: 31

His Xaa Gln Gly Thr Phe Thr Ser Asp Lys Ser Lys Tyr Leu Glu Ser
1               5                   10                  15

Glu Arg Ala Lys Glu Phe Val Glu Trp Leu Val Lys Glu Gly Gly Pro
            20                  25                  30

Ser Ser Gly
        35

<210> SEQ ID NO 32
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Aib
<220> FEATURE:
<221> NAME/KEY: BINDING
<222> LOCATION: (17)..(17)
<223> OTHER INFORMATION: amino group of Lysine is modified

<400> SEQUENCE: 32

His Xaa Gln Gly Thr Phe Thr Ser Asp Tyr Ser Lys Tyr Leu Glu Glu
1               5                   10                  15

Lys Arg Ala Arg Glu Phe Val Glu Trp Leu Leu Glu Ala Gly Gly Pro
            20                  25                  30

Ser Ser Gly
      35

<210> SEQ ID NO 33
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Aib
<220> FEATURE:
<221> NAME/KEY: BINDING
<222> LOCATION: (10)..(10)
<223> OTHER INFORMATION: amino group of Lysine is modified

<400> SEQUENCE: 33

His Xaa Gln Gly Thr Phe Thr Ser Asp Lys Ser Lys Tyr Leu Glu Glu
1               5                   10                  15

Arg Ala Ala Lys Glu Phe Ile Ala Trp Leu Leu Glu Gly Gly Pro Ser
            20                  25                  30

Ser Gly

<210> SEQ ID NO 34
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Aib
<220> FEATURE:
<221> NAME/KEY: BINDING
<222> LOCATION: (10)..(10)
<223> OTHER INFORMATION: amino group of Lysine is modified

<400> SEQUENCE: 34

His Xaa Gln Gly Thr Phe Thr Ser Asp Lys Ser Lys Tyr Leu Glu Glu
1               5                   10                  15

Arg Ala Ala Lys Glu Phe Val Glu Trp Leu Leu Glu Ala Gly Gly Pro
            20                  25                  30

Ser Ser Gly
        35

<210> SEQ ID NO 35
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MUTAGEN
<222> LOCATION: (2)..(2)
<223> OTHER INFORMATION: Xaa is Aib
<220> FEATURE:
<221> NAME/KEY: BINDING
<222> LOCATION: (20)..(20)
<223> OTHER INFORMATION: amino group of Lysine is modified

<400> SEQUENCE: 35

His Xaa Gln Gly Thr Phe Thr Ser Asp Tyr Ser Lys Tyr Leu Glu Glu
1               5                   10                  15

Lys Arg Ala Lys Glu Phe Val Glu Trp Leu Leu Glu Ala Gly Gly Pro

```
                    20                  25                  30
Ser Ser Gly
        35

<210> SEQ ID NO 36
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein X at position 2 is defined as Ser,
      D-Ser or Aib
<220> FEATURE:
<221> NAME/KEY: MISC_FEATURE
<222> LOCATION: (10)..(10)
<223> OTHER INFORMATION: Wherein X at position 10 is defined as Lys or
      Tyr
<220> FEATURE:
<221> NAME/KEY: MISC_FEATURE
<222> LOCATION: (12)..(12)
<223> OTHER INFORMATION: Wherein X at position 12 is defined as Lys or
      Arg
<220> FEATURE:
<221> NAME/KEY: MISC_FEATURE
<222> LOCATION: (15)..(15)
<223> OTHER INFORMATION: Wherein X at position 15 is defined as Asp or
      Glu
<220> FEATURE:
<221> NAME/KEY: MISC_FEATURE
<222> LOCATION: (16)..(16)
<223> OTHER INFORMATION: Wherein X at position 16 is defined as Ser or
      Glu
<220> FEATURE:
<221> NAME/KEY: MISC_FEATURE
<222> LOCATION: (17)..(17)
<223> OTHER INFORMATION: Wherein X at position 17 is defined as Arg, Glu
      or Lys
<220> FEATURE:
<221> NAME/KEY: MISC_FEATURE
<222> LOCATION: (18)..(18)
<223> OTHER INFORMATION: Wherein X at position 18 is defined as Lys, Ala
      or Arg
<220> FEATURE:
<221> NAME/KEY: MISC_FEATURE
<222> LOCATION: (20)..(20)
<223> OTHER INFORMATION: Wherein X at position 20 is defined as Arg or
      Lys
<220> FEATURE:
<221> NAME/KEY: MISC_FEATURE
<222> LOCATION: (23)..(23)
<223> OTHER INFORMATION: Wherein X at position 23 is defined as Val or
      Ile
<220> FEATURE:
<221> NAME/KEY: MISC_FEATURE
<222> LOCATION: (24)..(24)
<223> OTHER INFORMATION: Wherein X at position 24 is defined as Ala, Glu
      or Lys
<220> FEATURE:
<221> NAME/KEY: MISC_FEATURE
<222> LOCATION: (27)..(27)
<223> OTHER INFORMATION: Wherein X at position 27 is defined as Leu, Val
      or absent
<220> FEATURE:
<221> NAME/KEY: MISC_FEATURE
<222> LOCATION: (28)..(28)
<223> OTHER INFORMATION: Wherein X at position 28 is defined as Ala,
      Gly, Lys, Glu, Z (Gly Gly Pro Ser Ser Gly) or absent
<220> FEATURE:
<221> NAME/KEY: MISC_FEATURE
<222> LOCATION: (29)..(29)
<223> OTHER INFORMATION: Wherein X at position 29 is defined as Ala,
      Glu, Arg, Gly or Z (Gly Gly Pro Ser Ser Gly)
<220> FEATURE:
<221> NAME/KEY: MISC_FEATURE
```

```
<222> LOCATION: (30)..(30)
<223> OTHER INFORMATION: Wherein X at position 30 is defined as Glu or Z
      (Gly Gly Pro Ser Ser Gly)
<220> FEATURE:
<221> NAME/KEY: MISC_FEATURE
<222> LOCATION: (31)..(31)
<223> OTHER INFORMATION: Wherein X at position 31 is defined as Z (Gly
      Gly Pro Ser Ser Gly) or absent

<400> SEQUENCE: 36

His Xaa Gln Gly Thr Phe Thr Ser Asp Xaa Ser Xaa Tyr Leu Xaa Xaa
1               5                   10                  15

Xaa Xaa Ala Xaa Glu Phe Xaa Xaa Trp Leu Xaa Xaa Xaa Xaa Xaa
            20                  25                  30

<210> SEQ ID NO 37
<211> LENGTH: 6
<212> TYPE: PRT
<213> ORGANISM: Artificial Sequence
<220> FEATURE:
<223> OTHER INFORMATION: Synthetic

<400> SEQUENCE: 37

Gly Gly Pro Ser Ser Gly
1               5

<210> SEQ ID NO 38
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein X at position 2 is defined as Ser or
      Aib
<220> FEATURE:
<221> NAME/KEY: MISC_FEATURE
<222> LOCATION: (10)..(10)
<223> OTHER INFORMATION: Wherein X at position 10 is defined as Lys or
      Tyr
<220> FEATURE:
<221> NAME/KEY: MISC_FEATURE
<222> LOCATION: (16)..(16)
<223> OTHER INFORMATION: Wherein X at position 16 is defined as Ser or
      Glu
<220> FEATURE:
<221> NAME/KEY: MISC_FEATURE
<222> LOCATION: (17)..(17)
<223> OTHER INFORMATION: Wherein X at position 17 is defined as Arg, Glu
      or Lys
<220> FEATURE:
<221> NAME/KEY: MISC_FEATURE
<222> LOCATION: (18)..(18)
<223> OTHER INFORMATION: Wherein X at position 18 is defined as Lys, Ala
      or Arg
<220> FEATURE:
<221> NAME/KEY: MISC_FEATURE
<222> LOCATION: (20)..(20)
<223> OTHER INFORMATION: Wherein X at position 20 is defined as Arg or
      Lys
<220> FEATURE:
<221> NAME/KEY: MISC_FEATURE
<222> LOCATION: (23)..(23)
<223> OTHER INFORMATION: Wherein X at position 23 is defined as Val or
      Ile
<220> FEATURE:
<221> NAME/KEY: MISC_FEATURE
<222> LOCATION: (24)..(24)
<223> OTHER INFORMATION: Wherein X at position 24 is defined as Ala, Glu
      or Lys
<220> FEATURE:
<221> NAME/KEY: MISC_FEATURE
```

```
<222> LOCATION: (27)..(27)
<223> OTHER INFORMATION: Wherein X at position 27 is defined as Leu or
      absent
<220> FEATURE:
<221> NAME/KEY: MISC_FEATURE
<222> LOCATION: (28)..(28)
<223> OTHER INFORMATION: Wherein X at position 28 is defined as Glu or
      absent
<220> FEATURE:
<221> NAME/KEY: MISC_FEATURE
<222> LOCATION: (29)..(29)
<223> OTHER INFORMATION: Wherein X at position 29 is defined as Ala
<220> FEATURE:
<221> NAME/KEY: MISC_FEATURE
<222> LOCATION: (30)..(30)
<223> OTHER INFORMATION: Wherein X at position 30 is defined as Z (Gly
      Gly Pro Ser Ser Gly)

<400> SEQUENCE: 38

His Xaa Gln Gly Thr Phe Thr Ser Asp Xaa Ser Lys Tyr Leu Glu Xaa
1               5                   10                  15

Xaa Xaa Ala Xaa Glu Phe Xaa Xaa Trp Leu Xaa Xaa Xaa Xaa
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Synthetic

<400> SEQUENCE: 39

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 40
<211> LENGTH: 10
<212> TYPE: PRT
<213> ORGANISM: Artificial Sequence
<220> FEATURE:
<223> OTHER INFORMATION: Synthetic

<400> SEQUENCE: 40

Gly Pro Ser Ser Gly Ala Pro Pro Pro Ser
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Lys Arg Asn Arg Asn Asn Ile Ala
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Glu Ala Gly Gly Pro Ser Ser Gly
```

```
<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Glu Gly Gly Pro Ser Ser Gly
1               5
```

GLUCAGON-DERIVED PEPTIDE AND USE THEREOF

CROSS-REFERENCES TO RELATED APPLICATIONS

This application is the National Stage of International Application No. PCT/CN2019/117715, filed Nov. 12, 2019, which claims priority to Chinese Application No. 2018113382182, filed Nov. 12, 2018, the disclosures of which are hereby incorporated by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 3053-P24USPNP_Seq_List_FINAL_20211129_ST25.txt. The text file is 28 KB; was created on Nov. 29, 2021, contains no new matter, and is being submitted via EFS-Web.

TECHNICAL FIELD

The invention belongs to the technical field of medical biology, and particularly relates to glucagon-derived peptides and use thereof.

BACKGROUND ART

Obesity is a risk factor for a variety of diseases, and has become a global public health problem. In particular, the incidence and progress of metabolic syndrome including type 2 diabetes mellitus (T2DM), cardiovascular disease, nonalcoholic fatty liver disease and other common diseases are closely related to obesity. A number of large-scale clinical studies have found that, compared to people of normal weight, the incidence of multiple cardiovascular and metabolic diseases in overweight, obese or severely obese people with BMI of 25.0-29.9 kg/m$^2$, 30.0-34.9 kg/m$^2$ and >35.0 kg/m$^2$ were 2, 5 and 15 times higher respectively (Lancet 2, e277-e285, 2017). Studies have shown that 80-90% of T2DM patients are overweight or obese, and modest weight loss (4-5 kg) is beneficial for the prevention and control of conditions, including reduction of morbidity, control of blood glucose and disability (mortality) (Curr. Med. Res. Opin. 2011, 27 (7), 1431-1438).

Diet control and exercise are the most desirable means of weight loss, but generally ineffective. Drug intervention for obesity has limited efficacy or multiple risks, including side effects of severe cardiovascular effects, psychotic symptoms caused by central nervous effects, and so on. To date, few drugs alone have been able to achieve weight loss in excess of 5-10%. Only SGLT2 inhibitors and GLP-1 receptor agonists in T2DM therapeutics have a benign effect on body weight management. The effect of bariatric surgery is remarkable, but the risk of surgery is high, and the long-term effect is still uncertain. Therefore, there is still a great clinical need for a drug for controlling body weight, and a drug having both a primary condition treatment effect and capable of safely and effectively controlling body weight is an ideal choice.

The body's blood glucose and energy regulation signaling system are maintained in a fine balance by a variety of factors, including different polypeptide hormones. Pro-glucagon is a precursor polypeptide with 158 amino acids, and is processed in different tissues to produce various pro-glucagon-derived peptides such as glucagon (GC), glucagon-like peptide-1, 2 (GLP-1, 2) and oxyntomodulin. These hormones are involved in the regulation of various physiological functions such as glucose homeostasis, insulin secretion, gastric emptying, intestinal growth and food intake. Therefore, the treatment of intestinal hormones based on pro-glucagon has become a research direction of great concern in the field of metabolic diseases.

GC is a derived peptide containing 29 amino acids corresponding to amino acids 33 to 61 of pro-glucagon. It is produced in pancreatic α cells and acts on the liver under stress conditions such as body's hunger and cold, and increases blood glucose level to the normal range through glycolysis and gluconeogenesis. In addition to the effect of increasing blood glucose, the results of animal and human experiments show that GC also has the effects of emitting heat, increasing satiety, lipolysis, fat oxidation, ketogenesis and so on. Long-term administration can improve energy metabolism, including weight loss, but these beneficial effects on energy metabolism cannot be applied because of its inherent effect of increasing blood glucose.

GLP-1 is a derived peptide containing 37 amino acid residues corresponding to amino acids 72 to 108 of pro-glucagon, which is secreted by intestinal L cells in the body's meal response. It acts on pancreatic β-cells to promote insulin secretion and antagonize GC receptors to inhibit the increase of blood glucose. GLP-1 receptor agonists have been developed to treat hyperglycemia in patients with diabetes, which can protect and proliferate islet cells while lowering blood glucose, slow down gastric emptying and inhibit food intake, and can effectively decrease body weight. There are seven GLP-1 receptor agonists on the market, including short-acting agents like exenatide, liraglutide, and lixisenatide (once/twice a day), as well as long-acting agents albiglutide, dulaglutide, Byuderon, and semaglutide (once a week). Although GLP-1 receptor agonists have safe and unique effects of lowering blood glucose, large doses are generally needed when they are used to lose body weight, and these drugs are prone to gastrointestinal side effects, poor tolerance and narrow treatment window under large doses. As a result, there still exists a need for more tolerable therapeutics that can effectively control blood glucose and reduce body weight.

Oxyntomodulin, (OXM) is a hormone produced in the intestine during the post-translational modification of pro-glucagon, which is secreted simultaneously with hormones such as GLP-1 from ileal L-cells during the meal reaction. The acute effects of OXM include gastric emptying, exocrine secretion of stomach and pancreas, inhibition of food intake, resting energy consumption and so on, which can produce weight-loss effect. Up to now, the specific receptor of OXM is not clear, but it has been found that OXM is an endogenous GCGR/GLP-1R double agonist, and its activity and potency against the two receptors are weaker than those of the natural ligands of each receptor. In animal and human experiments, it has been found that peripheral administration of OXM can reduce food intake, cause weight loss, and increase metabolic rate, especially activity-related energy consumption in obese subjects. In particular, in clinical trials, the incidence of common gastrointestinal side effects such as nausea and vomiting were low when OXM was given peripherally in large doses to reduce body weight. Therefore, the treatment based on OXM or GLP-1/GCGR dual agonists shows potential application value for obesity and obese diabetes, but so far, no related drugs have been put on the market.

SUMMARY OF THE INVENTION

One object of the present invention is to provide a polypeptide derivative of glucagon, which is a variant designed from natural sequence of GC, and has a synergistic effect on energy metabolism through the double activation of GC/GLP-1 receptors, which can effectively lower blood glucose, reduce body weight and improve body fat level. It has more advantages than GLP-1 monoreceptor agonists in improving the disease state of diabetes, obesity, metabolic syndrome, non-alcoholic fatty liver, and so on.

It is another object of the present invention to provide a pharmaceutical composition comprising a glucagon polypeptide derivative of the present invention.

It is a further object of the present invention to provide use of a glucagon polypeptide derivative of the present invention.

The objects of the present invention are achieved by the following technical solutions.

In one aspect, the invention provides a polypeptide derivative, a modified derivative or a salt thereof, comprising a polypeptide having a sequence of following general formula I:

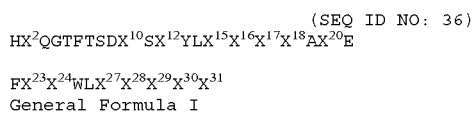

General Formula I wherein:
$X^2$ is Ser, D-Ser or Aib;
$X^{10}$ is Lys or Tyr;
$X^{12}$ is Lys or Arg;
$X^{15}$ is Asp or Glu;
$X^{16}$ is Ser or Glu;
$X^{17}$ is Arg, Glu or Lys;
$X^{18}$ is Lys, Ala or Arg;
$X^{20}$ is Arg or Lys;
$X^{23}$ is Val or Ile;
$X^{24}$ is Ala, Glu or Lys;
$X^{27}$ is Leu, Val or absent;
$X^{28}$ is Ala, Gly, Lys, Glu, Z or absent;
$X^{29}$ is Ala, Glu, Arg, Gly or Z;
$X^{30}$ is Glu or Z;
$X^{31}$ is Z or absent;
Z is fragment peptide GGPSSG (SEQ ID NO:37), and one and only one of $X^{28}$, $X^{29}$, $X^{30}$ and $X^{31}$ is Z; C-terminal carboxyl group is free or amidated; and
Meanwhile, one and only one of $X^{10}$, $X^{17}$, $X^{20}$ and $X^{24}$ is Lys with a side chain being modified.

Further, the invention provides a polypeptide derivative, or a modified derivative or a salt thereof, comprising a polypeptide having a sequence of the following general formula Ia):

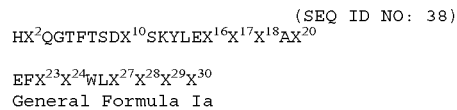

General Formula Ia wherein,
$X^2$ is Ser or Aib;
$X^{10}$ is Tyr or Lys;
$X^{16}$ is Ser or Glu;
$X^{17}$ is Arg, Glu or Lys;
$X^{18}$ is Lys, Ala or Arg;
$X^{20}$ is Arg or Lys;
$X^{23}$ is Val or Ile;
$X^{24}$ is Ala, Glu or Lys;
$X^{27}$ is Len or absent;
$X^{28}$ is Glu or absent;
$X^{29}$ is Ala;
$X^{30}$ is Z, and Z is a fragment peptide GGPSSG (SEQ ID NO:37);
one and only one of $X^{10}$, $X^{17}$, $X^{20}$ and $X^{24}$ is Lys with a side chain being modified; and C-terminal carboxyl group is free or amidated.

In preferred embodiments of the invention, in the general formula Ia),
$X^2$ is Aib;
$X^{10}$ is Lys or Tyr;
$X^{16}$ is Glu;
$X^{17}$ is Arg or Lys;
$X^{18}$ is Ala, Lys or Arg;
$X^{20}$ is Lys;
$X^{27}$ is absent;
$X^{28}$ is Glu;
$X^{29}$ is Ala;
$X^{30}$ is Z;
one and only one of $X^{10}$ and $X^{20}$ is Lys with a side chain being modified; and
C-terminal carboxyl group is free or amidated.

In some preferred embodiments, the general formula Ia) comprises a combination of the following amino acid sequences:
$X^{17}$ is Arg and $X^{18}$ is Ala;
$X^{17}$ is Arg and $X^{18}$ is Lys; or
$X^{17}$ is Lys and $X^{18}$ is Arg.

In preferred embodiments, the general formula Ia) comprises a combination of the following amino acid sequences:
$X^{23}$ is Val and $X^{24}$ is Ala or Glu; or
$X^{23}$ is Ile and $X^{24}$ is Ala or Glu.

In preferred embodiments of the invention, the polypeptide derivative comprises a polypeptide having a sequence selected from any one of SEQ ID NOs. 4-15.

In other preferred embodiments of the present invention, polypeptides having the structure of general formula I are provided, wherein in the general formula I,
$X^2$ is Aib;
$X^{10}$ is Lys or Tyr;
$X^{16}$ is Glu;
$X^{17}$ is Arg or Lys;
$X^{18}$ is Ala, Lys or Arg;
$X^{20}$ is Arg or Lys;
$X^{27}$ is absent;
$X^{28}$ is absent;
$X^{29}$ is Glu;
$X^{30}$ is Z;
$X^{31}$ is absent;
one and only one of $X^{10}$ and $X^{20}$ is Lys with a side chain being modified; and
C-terminal carboxyl group is free or amidated.

In preferred embodiments of the invention, the general formula I comprises a combination of the following amino acid sequences:
$X^{17}$ is Arg and $X^{18}$ is Ala;
$X^{17}$ is Arg and $X^{18}$ is Lys; or
$X^{17}$ is Lys and $X^{18}$ is Arg.

In further preferred embodiments of the invention, the general formula I comprises a combination of the following amino acid sequences: $X^{23}$ is Val and $X^{24}$ is Ala or Glu; or $X^{23}$ is Ile and $X^{24}$ is Ala or Glu.

In preferred embodiments of the invention, the polypeptide derivative comprises a polypeptide having a sequence selected from any one of SEQ ID NOs. 16-27.

In preferred embodiments of the invention, the polypeptide derivative is characterized in that $X^{10}$ is Tyr when $X^{20}$ is Lys with a side chain being modified.

In some embodiments of the present invention, the Lys with a side chain being modified means that the side chain ε-amino group of the Lys is modified by coupling a fatty acid through a hydrophilic linker fragment.

Preferably, the hydrophilic linker fragment used to modify the side chain ε-amino group of Lys is selected from a fragment consisting of one or more of Glu, γGlu, Gly and Ado (8-amino-3, 6-dioxaoctanoic acid), preferably γGlu-γGlu-, Glu-γGlu-, γGlu-Glu-, γGlu-Gly-Gly, γGlu-Gly-γGlu-, γGlu-Ado-Ado-; Ado-Ado-γGlu- or γGlu-Ado-Ado-γGlu-.

In preferred embodiments of the invention, the fatty acid is a C14-20 fatty acid, more preferably a C16-20 fatty diacid.

In another aspect, the invention provides a pharmaceutical composition comprising a polypeptide derivative, or modified derivative or salt thereof according to the invention.

Preferably, the pharmaceutical composition further comprises one or more pharmaceutically acceptable excipients. The pharmaceutically acceptable excipients comprise carrier, diluent, water-soluble filler, pH regulator, stabilizer, water for injection, osmotic pressure regulator and the like.

Preferably, the water-soluble filler includes, but is not limited to, mannitol, low molecular dextran, sorbitol, polyethylene glycol, glucose, lactose, galactose, and the like; the pH regulator includes, but is not limited to, organic or inorganic acids such as citric acid, phosphoric acid, lactic acid, tartaric acid, hydrochloric acid, and the like, or physiologically acceptable inorganic bases or salts such as potassium hydroxide, sodium hydroxide, ammonium hydroxide, sodium carbonate, potassium carbonate, ammonium carbonate, potassium bicarbonate, sodium bicarbonate, ammonium bicarbonate salts, and the like; the stabilizer include but is not limited to, EDTA-2Na, sodium thiosulfate, sodium pyrosulfite, sodium sulfite, dipotassium phosphate, sodium bicarbonate, sodium carbonate, arginine, lysine, glutamic acid, aspartic acid, polyethylene glycol, polyvinyl alcohol, polyvinylpyrrolidone, carboxy/hydroxycellulose or derivatives thereof such as HPC, HPC-SL, HPC-L or HPMC, cyclodextrin, sodium lauryl sulfate or trihydroxymethyl aminomethane, and the like; the osmotic pressure regulator includes, but is not limited to, sodium chloride or potassium chloride.

Preferably, the pharmaceutical composition of the invention can be administered in the form of intravenous, muscular or subcutaneous injections, or administered orally, rectum or intra nasally. The dosage may range from 5 μg to 10 mg/time, depending on the subject to be treated, the mode of administration, the indication and other factors.

In a further aspect, the invention provides use of a polypeptide derivative, modified derivative or salt thereof of the invention in the preparation of a medicament for the treatment of a metabolic disease, preferably the described metabolic disease is diabetes, obesity, fatty liver, hyperlipidemia and/or metabolic syndrome; and more preferably, the fatty liver is non-alcoholic fatty liver.

In another aspect, the invention provides a method for treating a metabolic disease comprising administering to the patients in need thereof a polypeptide derivative, modified derivative or salt thereof of the invention, preferably the metabolic disease is diabetes, obesity, fatty liver, hyperlipidemia and/or metabolic syndrome; and more preferably, the fatty liver is non-alcoholic fatty liver.

Compared with GLP-1 monoreceptor agonist, the polypeptide derivatives provided by the invention have the effects of promoting weight loss and preventing weight gain while lowering blood glucose more effectively, reverse insulin resistance, and have unexpected beneficial effects compared with the existing medicine.

Structure of glucagon-derived peptide: Endogenous GLP-1 is a derivative peptide containing 30-31 amino acid residues (7-36/37) corresponding to amino acids 72 to 108 of pro-glucagon with the amino acid sequence HAEGTFTSDVSSYLEGQAAKEFIAWLVKGR (7-36) (SEQ ID NO. 1), HAEGTFTSDVSSYLEGQAAKEFIAWLVKGRG (7-37) (SEQ ID NO:39), and the C-terminus free or amidated. Endogenous GC is a derivative peptide containing 29 amino acids corresponding to amino acids 33 to 61 of pro-glucagon, with the amino acid sequence of HSQGTFTSDYSKYLDSRRAQDFVQWLMNT (SEQ ID NO. 2), and the C-terminal carboxyl group free. Native GLP-1 and GC have 47% of homology in the amino acid sequences (Andreas Evers et al., J. Med. Chem. 2017, 60, 4293-4303), the N-terminal sequences of both are highly conserved. GLP-1 is highly selective for its receptor, and GC is also a weak agonist of the GLP-1 receptor. Therefore, it is feasible to design GLP-1/GCGR dual agonists based on GC sequences.

The amino acid sequence of OXM is HSQGTFTSDYSKYLDSRRAQDFVQWLMNTKRNRNNIA (SEQ ID NO. 3), which comprises the original sequence of GC (1-29), and an intervening peptide-1 (IP-1, 30-37) corresponding to the pro-glucagon amino acid sequence 82-89. OXM has dual agonistic activity on GC/GLP-1R, suggesting that adjustment of the C-terminal sequence of the GC sequence might have benefit on achieving a potency balance for GC/GLP-1R. In the published patent documents, for example, in CN200980132562.9, CN201080027026.5, CN201680062196.4, variants of the original sequence of GC (1-29) is extended at C-terminal with the C-terminal 10 peptide (GPSSGAPPPS (SEQ ID NO:40) abbreviated as Cex) sequence of Exendin-4. CN201680036771.3, however, chooses a design scheme for replacing the C-terminal insertion peptide (KRNRNNIA) (SEQ ID NO:41) of the OXM sequence with the GGPSSG (SEQ ID NO:37) peptide. The prior art all adopted a design idea that mutation of some sites is carried out on the basis of keeping a GC full-length sequence (1-29), and then extending the sequence with different peptide fragments.

The C-terminal changes of the polypeptide based on the GC sequence are very sensitive to the recognition of the GC/GLP-1 receptor, especially to the activity of the GC receptor. Thus, it is generally believed that retention of the C-terminus of the GC sequence is important for retention of GC receptor agonistic activity. The prior art generally adopts mutation of individual sites on the basis of keeping the GC full-length sequence (1-29), which is basically a reasonable replacement rule known in the art: for example, 21Asp is replaced by Glu, 24Gln is retained or replaced by Glu, sensitive amino acids in the C-terminal fragment 27-29 such as 27Met is replaced by Leu, and 28Asn is replaced by Glu or Ala. The present inventors have found in study that even with these conservative approaches followed by C-terminal extension and fatty acyl modifications, it is difficult to predict that a GC/GLP-1 receptor dual-receptor agonists with balanced potency can be obtained. Meanwhile, it is also found that these strategies are not helpful for improving the hydrophobicity of the polypeptide, especially under the condition of long-chain fatty acyl modification, difficulties of synthesis and preparation are not improved, the preparation cost is increased, the solubility of the final product is poor, and the operability of the preparations is influenced.

Different from the prior art scheme, in the technical scheme provided by the invention, only 1-26 peptide segments of the GC sequence are reserved in the design of the polypeptide main chain, the C-terminal is appropriately extended on the basis of reasonable mutation of individual sites, and then fatty acyl modification measures are adopted to obtain the GC/GLP-1 receptor dual-receptor agonist with balanced activity potency ratio and good solubility and stability.

In certain embodiments of the present invention, rational substitutions at positions 16-20 of the GC (1-26) sequence, such as substituting 16Ser with Glu, 18Arg with Ala or Lys, and 20Gln with Lys, are well known in the art to facilitate improved GLP-1 receptor selectivity. In yet other specific embodiments, position 24Gln is replaced with Glu to modulate the charge distribution of the corresponding peptide fragment. In the technical scheme disclosed in the prior art, 27Met of a GC sequence is generally replaced by a neutral or positively charged amino acid, such as Leu and Lys, and the corresponding position of the polypeptide sequence provided by the preferred technical scheme of the invention is a Glu residue, and then Ala is inserted or the C-terminus is directly extended by a peptide segment (GGPSSG) (SEQ ID NO:37) containing hydrophilic amino acid residues to obtain a main chain sequence. For example, the main chain sequence of compounds 1, 2; compounds 4-7; compounds 10-15; compounds 21, 22; compounds 27-39; and compounds 41-81 in Example 1.

Fatty acyl modifications are well known in the art as long-acting techniques for polypeptides. In an embodiment of the invention, the fatty acyl group on the side chain of Lys at a specific position in the active peptide sequence is modified by a hydrophilic linker arm. In certain embodiments, the lysine residue is at position 10, and in certain embodiments, the modification site is at position 20. In order to improve the solubility of the modified polypeptide and maintain the flexibility of the polypeptide structure, it is necessary to link the polypeptide and the fatty acyl modifying radical group with a hydrophilic linker arm. In certain embodiments of the invention, the hydrophilic linker arm is -γ-Glu-γ-Glu-, in other embodiments, the hydrophilic linker arm is -γ-Glu-Ado-Ado-γ-Glu; or in other embodiments, the hydrophilic linker arm is -Ado-Ado-γ-Glu. The fatty acyl group is preferably a mono-fatty acid or a fatty diacid of C16-20. In certain embodiments, the fatty acyl group is a C16 or C18 acyl group; In certain particular embodiments, the fatty acyl group is C18, C20 diacid monoacyl.

Generally, it is beneficial to maintain homology by making as few changes as possible to the native sequence, but there are many druggability problems with the endogenous pro-glucagon sequence: N-terminal dipeptides are easily recognized by dipeptide kininase in vivo and are hydrolytically inactivated, resulting in a short plasma half-life (≤12 min); the physical properties are unstable, i.e. the isoelectric point (pI) is 7.6, it is neutral and hydrophobic, has poor solubility and is easy to aggregate and precipitate in solution; and the sequence contains Met, Asp, Asn and other amino acids that are prone to oxidation or racemization, resulting in unstable chemical properties.

In order to improve the metabolic stability of the polypeptide, in a preferred embodiment of the present invention, 2Ser is generally replaced with Aib or D-Ser to ensure sustained exertion of polypeptide activity. Meanwhile, in a preferred embodiment of the invention, sensitive amino acids in the GC sequence are further replaced, such as 15, 21Asp is replaced by Glu, and the adjusted C-terminal peptide segment does not contain sensitive amino acid residues such as Met, Gln, Asn and the like, so that the chemical stability is greatly improved. Thus, the above-described adjustments and improvements have multiple beneficial effects on the improvements of the activity balance and physicochemical properties, with significant advantages over the prior art.

The invention provides GLP-1/glucagon dual agonistic peptides, which have the following activity characteristics through the above structural design of the present invention: the polypeptides provided by the invention have at least 1% receptor agonistic activity compared with a natural ligand of each receptor of GLP-1/GCGR. By a series of structural optimization designs, the intensity of agonistic action on the GLP-1 receptor is comparable to or equivalent to 150%, 200%, 300%, 500%, 1000% or more of that of the endogenous native ligand GLP-1 (7-36/37). The agonist activity on the glucagon receptor is comparable to the endogenous ligand (GC) or equivalent to 10-1000% of the intensity of action of the endogenous agonist. In certain embodiments, the polypeptides provided herein have receptor agonistic activity equal to or greater than that of an endogenous ligand. In other embodiments, the agonistic action on the GLP-1 receptor is stronger than the agonistic action on the glucagon receptor, or the agonistic actions on both receptors are equally strong. The relative intensities of activity on the GLP-1 and glucagon receptors can be expressed in terms of potency ratios, i.e. the potency ratios of a polypeptide comprising a sequence of general formula I provided herein for the GLP-1/glucagon receptor include, but are not limited to, 10:1, 9:1, 8:1, 7:1, 6:1, 3:1, 1:1 to 1:10.

The basic peptide chain of the polypeptide derivatives with the structure of the general formula I provided by the invention can be prepared by a method well known in the art:

1) synthesized in a stepwise manner through conventional solid or liquid phase methods or by fragment assembly;
2) expressing nucleic acid constructors encoding peptides in host cells and recovering expression products from host cell culture;
3) influencing cell-free in vitro expression of nucleic acid constructors encoding polypeptides and recovering expressed products;
or through any combination of methods 1), 2) or 3) to obtain peptide fragments, and then connect these fragments to obtain the target peptide.

Preferably, in the embodiments provided herein, the target peptide is prepared using Fmoc solid phase synthesis methods, which are well known to those skilled in the art.

Substituents may be introduced stepwise synthetically by the peptide synthesis steps described above. Substituents with appropriate protecting groups are used, such as Fmoc-8-amino-3, 6 dioxaoctanoic acid, and Fmoc-γ-Glu-OtBu. The introduction of fatty chain moieties, especially fatty diacid monoester acyl groups, can be accomplished using, but not limited to, C18, C20 mono-tert-butyl alkanoate. After each coupling step, the unreacted intermediates can be blocked using excess acetic anhydride and pyridine. The ε-amino group of the modifiable Lys may be protected by using Mtt or Dde.

Purification: following the conjugation reaction, the target product may be separated by suitable methods known in the art. Suitable methods include, but are not limited to, ultrafiltration, dialysis, chromatography, and the like. Preparative high performance liquid chromatography purification is preferably employed in embodiments of the present invention.

Receptor activity assay: in the embodiments of the invention the effect of the polypeptides on the GLP-1/GC receptor is assessed by the effect of GLP-1/GC receptor mediated cAMP production in vitro.

Regulation of body weight and blood glucose: according to the embodiments of the invention, the influence of the polypeptides provided by the invention on body weight and blood glucose is evaluated by using a high-fat diet obese diabetic mouse (Dio) model, and the result shows that the polypeptide derivatives provided by the invention have remarkable effect on body weight loss and blood glucose lowering, and the effect of body weight loss is obviously superior to that of a positive control drug. It is suggested that it has potential advantages in preparing drugs for the control of obesity and other metabolic diseases and the treatment of diabetes.

BRIEF DESCRIPTION OF THE DRAWINGS

Hereinafter, embodiments of the present invention will be described in detail with reference to the accompanying drawings, in which:

FIG. 1 shows the effect of compounds 1, 4, 6 and 22 on the body weight of Dio mice in Example 3, where sample numbers 1 #-4 # are compound 1, compound 4, compound 6 and compound 22, respectively.

DETAILED DESCRIPTION OF THE INVENTION

The present invention will be further described below in conjunction with specific embodiments. The examples are merely illustrative of the invention and are not intended to limit the invention in any way.

Description of Amino Acid Abbreviations

Gly: Glycine (G)
Ala: Alanine (A)
Val: Valine (V)
Leu: Leucine (L)
Phe: Phenylalanine (F)
Trp: Tryptophan (W)
Ser: Serine (S)
Thr: Threonine (T)
Glu: Glutamic acid (E)
Gln: Glutamine (Q)
Asp: Aspartic acid (D)
Asn: Asparagine (N)
Tyr: Tyrosine (Y)
Arg: Arginine (R)
Lys: Lysine (K)
His: Histidine (H)
Aib: α-aminoisobutyric acid
Ado: 8-amino-3, 6-dioxaoctanoic acid
Description of reagent abbreviations
Boc: Tert-butoxycarbonyl
Tert-Bu: Tert-butyl
DCM: Dichloromethane
DIC: diisopropylcarbodiimide
Fmoc: 9-fluorenylmethoxycarbonyl
HoBt: 1-Hydroxybenzotriazole
HBTU: 2-(1H-benzotriazol-1-yl)-1, 1, 3, 3-tetramethyl-uronium hexafluorophosphate
HATU: 0-(7-azabenzotriazol-1-yl)-N, N, N', N'-tetramethyl-uronium hexafluorophosphate
Mtt: 4-methyltriphenylmethyl
NMP: N-methylpyrrolidone
DMF: dimethylformamide
Pbf: 2, 2, 4, 6, 7-pentamethyldihydrobenzofuran
Dde: 1-(4, 4-dimethyl-2, 6-dioxocyclohexylidene)-3-methyl-butyl
Trt: Triphenylmethyl
EDT: Ethanedithiol
TFA: Trifluoroacetic acid
TIS: Triisopropylsilane
FBS: Fetal bovine serum Example 1

Basic linear sequence of the polypeptides and the side chain modified peptide derivatives provided by the invention are prepared according to the following general method:

1) Synthesis: Using Fmoc strategy, synthesizing gradually with a PSI200 type polypeptide synthesizer according to the following steps:

a) coupling the resin solid-phase carrier and the Fmoc-protected C-terminal amino acid in the presence of an activator system to obtain Fmoc-amino acid-resin; wherein, amino resins such as Rink Amide AM, Rink Amide, Rink MBHA and the like are adopted for synthesizing the C-terminal amidated polypeptide; the ratio of Fmoc-amino acid to resin (mol/mol) was 3-5:1 and coupling activators were HOBT/DIC or HOBT/HBTU/DIEA.

b) Peptide chain elongation: assembling amino acids according to amino acid sequence of the peptide through the solid phase synthesis method to obtain peptide-resin conjugate with N-terminal and side chain protection; Following protection strategies were employed for the amino acid residues with side chain: protecting tryptophan with Boc, glutamic acid with OtBu, lysine with Boc, glutamine with Trt, tyrosine with tBu, serine with Trt or tBu, aspartic acid with OtBu, threonine with tBu, cysteine with Trt, arginine with Pbf, α-amino group of histidine (Trt) is protected with Boc, and ε-amino group of modifiable lysine is protected with Dde. Using HOBT/DIC, HOBT/HBTU/DIEA and HOBT/HATU/DIEA as coupling agents, the end point of the reaction was detected by ninhydrin method, and using 20% piperidine in NMP (DMF) as the deprotection reagent.

c) Deprotection of ε-amino group of lysine:
the fully protected polypeptide-resin synthesized in the above steps was washed with NMP-DCM (1:1 V/V) for three times, then a freshly prepared solution of 2.0% hydrazine hydrate in NMP was added, stirred at room temperature for 12.0 min, filtered, repeated twice, and the resin was washed for three times with each of DCM and NMP.

d) Modification of lysine side chain:
after the deprotection of ε-amino group of lysine, Fmoc-Ado or Fmoc-γ-Glu (tBu) and HOBt/HBTU, DIEA in a ratio of (resin:linker 1:4-5 (mol/mol)) were added and stirred for 2.0-4.0 h to react, then Fmoc was deprotected and the linker arm and fatty acyl groups of the desired chain length were continued to be linked in the same manner. If the reaction was not completed after repeating twice, excessive acetic anhydride/pyridine was added to block and the reaction was continued to the next step.

e) Polypeptide cleavage: the fully protected peptide-resin was washed with NMP and then washed 3-6 times with DCM to remove NMP, then TFA/EDT/TIS/H2O (92.5:2.5:2.5:2.5 v/v) solution was added and stirred at room temperature under nitrogen protection for 90 min to deprotect and de-resin. Performing suction filtration to obtain filtrate, precipitating the crude polypeptide by using excess ice ethyl ether, centrifuging, collecting the precipitate, washing the precipitate with a small amount of ethyl ether, and drying under vacuum to obtain crude polypeptide.

2) Purification: the crude peptide was dissolved in water or 10-15% acetonitrile (10-50 mg/ml), separated and purified by preparative HPLC method with C8 or C18 chromatographic column and acetonitrile-water-trifluoroacetic acid system, then concentrated and lyophilized to obtain pure peptide (purity ≥97%).

The polypeptide derivatives with the following structures were prepared by the above mentioned method.

TABLE 1

Compounds synthesized

| Compound No. | Sequence No. | Sequence |
|---|---|---|
| 1 | SEQ ID NO. 4 | HAibQGTFTSDK*SKYLEERAAKEFIAWLEAGGPSSG-Amid |
| 2 | SEQ ID NO. 11 | HAibQGTFTSDK*SKYLEERAAKEFVEWLEAGGPSSG-Amid |
| 3 | SEQ ID NO. 29 | HAibQGTFTSDK*SKYLEERAAKEFVAWLKEGGPSSG-Amid |
| 4 | SEQ ID NO. 11 | HAibQGTFTSDK*SKYLEERAAKEFVAWLEAGGPSSG-Amid |
| 5 | SEQ ID NO. 23 | HAibQGTFTSDK*SKYLEERAAKEFVEWLEGGPSSG-Amid |
| 6 | SEQ ID NO. 16 | HAibQGTFTSDK**SKYLEERAAKEFIAWLEGGPSSG-Amid |
| 7 | SEQ ID NO. 23 | HAibQGTFTSDK*SKYLEERAAKEFVEWLEGGPSSG-Amid |
| 8 | SEQ ID NO. 32 | HAibQGTFTSDYSKYLEEK*RAREFVEWLLEAGGPSSG-Amid |
| 9 | SEQ ID NO. 28 | HAibQGTFTSDYSKYLEEK*RAREFVAWLLEGGPSSG-Amid |
| 10 | SEQ ID NO. 13 | HAibQGTFTSDK*SKYLEERKAKEFIAWLEAGGPSSG-Amid |
| 11 | SEQ ID NO. 14 | HAibQGTFTSDK*SKYLEEKRAKEFIEWLEAGGPSSG-Amid |
| 12 | SEQ ID NO. 15 | HAibQGTFTSDK*SKYLEEKRAKEFVEWLEAGGPSSG-Amid |
| 13 | SEQ ID NO. 11 | HAibQGTFTSDK***SKYLDERAAKEFVAWLEAGGPSSG-Amid |
| 14 | SEQ ID NO. 17 | HAibQGTFTSDYSKYLEERAAK**EFIEWLEGGPSSG-Amid |
| 15 | SEQ ID NO. 6 | HAibQGTFTSDYSKYLDERAAK*EFVAWLEAGGPSSG-Amid |
| 16 | SEQ ID NO. 33 | HAibQGTFTSDK*SKYLEERAAKEFIAWLLEGGPSSG-Amid |
| 17 | SEQ ID NO. 29 | HAibQGTFTSDK**SKYLEERAAKEFVAWLKEGGPSSG-Amid |
| 18 | SEQ ID NO. 30 | HAibQGTFTSDK* SKYLEERAAKEFVEWLVKGEGGPSSG-Amid |
| 19 | SEQ ID NO. 31 | HAibQGTFTSDK*SKYLESERAKEFVEWLVKEGGPSSG-Amid |
| 20 | SEQ ID NO. 32 | HAibQGTFTSDYSKYLEEK*RAREFVEWLLEAGGPSSG-Amid |

TABLE 1-continued

Compounds synthesized

| Compound No. | Sequence No. | Sequence |
|---|---|---|
| 21 | SEQ ID NO. 16 | HAibQGTFTSDK*SKYLEERAAKEFIAWLEGGPSSG-Amid |
| 22 | SEQ ID NO. 11 | HAibQGTFTSDK**SKYLEERAAKEFVAWLEAGGPSSG-Amid |
| 23 | SEQ ID NO. 14 | HAibQGTFTSDK**SKYLDEKRAKEFIEWLEAGGPSSG-Amid |
| 24 | SEQ ID NO. 11 | HAibQGTFTSDK**SKYLDERAAKEFVAWLEAGGPSSG-Amid |
| 25 | SEQ ID NO. 34 | HAibQGTFTSDK*SKYLEERAAKEFVEWLLEAGGPSSG-Amid |
| 26 | SEQ ID NO. 35 | HAibQGTFTSDYSKYLEEKRAK*EFVEWLLEAGGPSSG-Amid |
| 27 | SEQ ID NO. 4 | HAibQGTFTSDK**SKYLEERAAKEFIAWLEAGGPSSG-Amid |
| 28 | SEQ ID NO. 5 | HAibQGTFTSDYSKYLEERAAK**EFIAWLEAGGPSSG-Amid |
| 29 | SEQ ID NO. 5 | HSQGTFTSDYSKYLDERAAK*EFIAWLEAGGPSSG-Amid |
| 30 | SEQ ID NO. 6 | HAibQGTFTSDYSKYLEERAAK**EFVAWLEAGGPSSG-Amid |
| 31 | SEQ ID NO. 6 | HAibQGTFTSDYSKYLEERAAK**EFVEWLEAGGPSSG-Amid |
| 32 | SEQ ID NO. 18 | HAibQGTFTSDYSKYLEERAAK**EFVEWLEGGPSSG-Amid |
| 33 | SEQ ID NO. 18 | HAibQGTFTSDYSKYLEERAAK**EFVAWLEGGPSSG-Amid |
| 34 | SEQ ID NO. 19 | HAibQGTFTSDYSKYLDERKAK**EFVAWLEGGPSSG-Amid |
| 35 | SEQ ID NO. 4 | HAibQGTFTSDK***SKYLEERAAKEFIAWLEAGGPSSG-Amid |
| 36 | SEQ ID NO. 4 | HSQGTFTSDK**SKYLDERAAKEFIAWLEAGGPSSG-Amid |
| 37 | SEQ ID NO. 5 | HSQGTFTSDYSKYLDERAAK**EFIAWLEAGGPSSG-Amid |
| 38 | SEQ ID NO. 17 | HSQGTFTSDYSKYLDERAAK**EFIAWLEGGPSSG-Amid |
| 39 | SEQ ID NO. 5 | HAibQGTFTSDYSKYLEERAAK***EFIAWLEAGGPSSG-Amid |
| 40 | SEQ ID NO. 10 | HAibQGTFTSDYSKYLEEKRAK*EFVEWLEAGGPSSG-Amid |
| 41 | SEQ ID NO. 7 | HAibQGTFTSDYSKYLEERKAK*EFVEWLEAGGPSSG-Amid |
| 42 | SEQ ID NO. 7 | HAibQGTFTSDYSKYLDERKAK**EFVEWLEAGGPSSG-Amid |
| 43 | SEQ ID NO. 7 | HAibQGTFTSDYSKYLEERKAK**EFVAWLEAGGPSSG-Amid |
| 44 | SEQ ID NO. 8 | HAibQGTFTSDYSKYLEERKAK**EFIAWLEAGGPSSG-Amid |
| 45 | SEQ ID NO. 8 | HAibQGTFTSDYSKYLDERKAK**EFIAWLEAGGPSSG-Amid |

TABLE 1-continued

Compounds synthesized

| Compound No. | Sequence No. | Sequence |
|---|---|---|
| 46 | SEQ ID NO. 8 | HAibQGTFTSDYSKYLDERKAK***EFIAWLEAGGPSSG-Amid |
| 47 | SEQ ID NO. 8 | HAibQGTFTSDYSKYLEERKAK***EFIAWLEAGGPSSG-Amid |
| 48 | SEQ ID NO. 10 | HAibQGTFTSDYSKYLEEKRAK**EFVAWLEAGGPSSG-Amid |
| 49 | SEQ ID NO. 9 | HAibQGTFTSDYSKYLEEKRAK**EFIAWLEAGGPSSG-Amid |
| 50 | SEQ ID NO. 9 | HAibQGTFTSDYSKYLDEKRAK**EFIAWLEAGGPSSG-Amid |
| 51 | SEQ ID NO. 9 | HAibQGTFTSDYSKYLDEKRAK***EFIEWLEAGGPSSG-Amid |
| 52 | SEQ ID NO. 9 | HAibQGTFTSDYSKYLEEKRAK***EFIAWLEAGGPSSG-Amid |
| 53 | SEQ ID NO. 10 | HAibQGTFTSDYSKYLEEKRAK**EFVAWLEAGGPSSG-Amid |
| 54 | SEQ ID NO. 10 | HAibQGTFTSDYSKYLEEKRAK**EFVEWLEAGGPSSG-Amid |
| 55 | SEQ ID NO. 10 | HAibQGTFTSDYSKYLDEKRAK*EFVEWLEAGGPSSG-Amid |
| 56 | SEQ ID NO. 9 | HAibQGTFTSDYSKYLEEKRAK*EFIEWLEAGGPSSG-Amid |
| 57 | SEQ ID NO. 9 | HAibQGTFTSDYSKYLDEKRAK*EFIAWLEAGGPSSG-Amid |
| 58 | SEQ ID NO. 10 | HAibQGTFTSDYSKYLEEKRAK*EFVEWLEAGGPSSG-Amid |
| 59 | SEQ ID NO. 9 | HAibQGTFTSDYSKYLDEKRAK*EFIEWLEAGGPSSG-Amid |
| 60 | SEQ ID NO. 12 | HAibQGTFTSDK*SKYLEERKAKEFVAWLEAGGPSSG-Amid |
| 61 | SEQ ID NO. 15 | HAibQGTFTSDK*SKYLEEKRAKEFVEWLEAGGPSSG-Amid |
| 62 | SEQ ID NO. 19 | HAibQGTFTSDYSKYLEERKAK*EFVEWLEGGPSSG-Amid |
| 63 | SEQ ID NO. 19 | HAibQGTFTSDYSKYLEERKAK**EFVEWLEGGPSSG-Amid |
| 64 | SEQ ID NO. 19 | HAibQGTFTSDYSKYLEERKAK**EFVAWLEGGPSSG-Amid |
| 65 | SEQ ID NO. 20 | HAibQGTFTSDYSKYLEERKAK**EFIAWLEGGPSSG-Amid |
| 66 | SEQ ID NO. 20 | HAibQGTFTSDYSKYLDERKAK**EFIEWLEGGPSSG-Amid |
| 67 | SEQ ID NO. 20 | HAibQGTFTSDYSKYLDERKAK***EFIEWLEGGPSSG-Amid |
| 68 | SEQ ID NO. 20 | HAibQGTFTSDYSKYLEERKAK***EFIAWLEGGPSSG-Amid |
| 69 | SEQ ID NO. 19 | HAibQGTFTSDYSKYLDERKAK*EFVEWLEGGPSSG-Amid |
| 70 | SEQ ID NO. 21 | HAibQGTFTSDYSKYLEEKRAK**EFIAWLEGGPSSG-Amid |

TABLE 1-continued

Compounds synthesized

| Compound No. | Sequence No. | Sequence |
|---|---|---|
| 71 | SEQ ID NO. 21 | HAibQGTFTSDYSKYLDEKRAK**EFIEWLEGGPSSG-Amid |
| 72 | SEQ ID NO. 21 | HAibQGTFTSDYSKYLDEKRAK***EFIAWLEGGPSSG-Amid |
| 73 | SEQ ID NO. 21 | HAibQGTFTSDYSKYLEEKRAK***EFIEWLEGGPSSG-Amid |
| 74 | SEQ ID NO. 22 | HAibQGTFTSDYSKYLEEKRAK**EFVAWLEGGPSSG-Amid |
| 75 | SEQ ID NO. 16 | HAibQGTFTSDK**SKYLDERAAKEFIAWLEGGPSSG-Amid |
| 76 | SEQ ID NO. 22 | HAibQGTFTSDYSKYLEEKRAK*EFVEWLEGGPSSG-Amid |
| 77 | SEQ ID NO. 4 | HAibQGTFTSDK***SKYLDERAAKEFIAWLEAGGPSSG-Amid |
| 78 | SEQ ID NO. 21 | HAibQGTFTSDYSKYLDEKRAK*EFIAWLEGGPSSG-Amid |
| 79 | SEQ ID NO. 4 | HSQGTFTSDK**SKYLDERAAKEFIAWLEAGGPSSG-Amid |
| 80 | SEQ ID NO. 21 | HAibQGTFTSDYSKYLEEKRAK*EFIEWLEGGPSSG-Amid |
| 81 | SEQ ID NO. 27 | HAibQGTFTSDK*SKYLEEKRAKEFVEWLEGGPSSG-Amid |

*-γE-γE-OC$_{16}$H$_{31}$
**-Ado-Ado-γE-OC$_{17}$H$_{32}$COOH
***-Ado-Ado-γE-OC$_{19}$H$_{36}$COOH

Example 2 Effect on GLP-1/GC Receptors

The effect of the polypeptide on the GLP-1/GC receptor is assessed by the effect of GLP-1/GC receptor mediated cAMP production in vitro.

Chinese guinea pig lung cells transfected with human GLP-1 receptor and HEK293 cells transfected with GC receptor were inoculated in 96-well plates (200,000 cells/well), washed with Hanks' balanced salt buffer, and co-incubated with different concentrations of test polypeptide samples ($10^{-5}$-$10^{-2}$ mol/L) for 20 min at 37° C. in the presence of 200 mmol/L 3-isobutyl-1-methyl alizarin. The medium was removed, the cells were lysed, and cAMP values were detected referring to the detection method described for the assay kit. The 50% effective concentration (EC50) was calculated by using Origin software. The results are illustrated in Table 2.

TABLE 2

Agonistic action of polypeptides on GLP-1/GC receptors

| Peptides | GLP-1R (nM EC$_{50}$) | GCGR (nM EC$_{50}$) |
|---|---|---|
| GLP-1 | 0.5614 | >100 |
| Glucagon (GCG) | >100 | 0.0499 |
| Compound 1 | 0.0654 | 0.0574 |
| Compound 2 | 0.219 | 0.0352 |
| Compound 3 | 20.75 | 0.10 |
| Compound 4 | 0.051 | 0.024 |
| Compound 5 | 0.260 | 0.193 |
| Compound 6 | 0.439 | 0.052 |
| Compound 7 | 0.720 | 0.026 |
| Compound 11 | 3.046 | 1.732 |
| Compound 13 | 0.076 | 0.033 |
| Compound 15 | 0.580 | 0.148 |
| Compound 16 | 0.405 | 0.092 |
| Compound 17 | 2.214 | 0.486 |
| Compound 19 | 3.527 | 6.250 |
| Compound 21 | 0.830 | 0.175 |
| Compound 22 | 0.027 | 0.018 |
| Compound 23 | 0.194 | 0.329 |
| Compound 25 | 0.211 | 0.278 |
| Compound 26 | 0.193 | 0.197 |
| Compound 27 | 0.011 | 0.014 |
| Compound 28 | 0.449 | 0.026 |
| Compound 32 | 1.015 | 0.077 |
| Compound 35 | 0.044 | 0.036 |
| Compound 36 | 0.072 | 0.069 |
| Compound 38 | 0.716 | 0.102 |
| Compound 42 | 0.520 | 0.024 |
| Compound 44 | 0.371 | 0.219 |
| Compound 50 | 0.119 | 0.048 |
| Compound 53 | 0.532 | 0.316 |
| Compound 54 | 0.219 | 0.274 |
| Compound 57 | 0.094 | 0.081 |
| Compound 62 | 0.313 | 0.156 |
| Compound 66 | 0.051 | 0.058 |
| Compound 68 | 0.130 | 0.314 |
| Compound 69 | 0.778 | 0.261 |

TABLE 2-continued

Agonistic action of polypeptides on GLP-1/GC receptors

| Peptides | GLP-1R (nM $EC_{50}$) | GCGR (nM $EC_{50}$) |
|---|---|---|
| Compound 74 | 0.842 | 0.725 |
| Compound 75 | 0.141 | 0.087 |
| Compound 76 | 0.220 | 0.191 |
| Compound 77 | 0.291 | 0.076 |
| Compound 79 | 0.033 | 0.025 |

The in vitro receptor agonistic activity results shown in Table 2 show that the polypeptide derivatives having the amino acid sequences of the present invention have the dual agonistic activity of the GLP-1/GC receptor, wherein the polypeptide derivatives having the C-terminal position 27 to the terminal sequence EAGGPSSG (SEQ ID NO:42) or EGGPSSG (SEQ ID NO:43), especially the former, have an activity intensity and potency ratio better than the polypeptide derivatives having other terminal sequences under the same conditions. Preferably, the potency ratio of the polypeptide derivative is in the equilibrium range of 10:1 to 1:10, and better dual agonistic activity of the GLP-1/GC receptor is achieved.

Example 3

Effects of Representative Compounds 1, 4, 6, 22 of Example 1 on Body Weight and Blood Glucose in Dio Mice 1) Effect on Body Weight C57BL/6J mice (n=35), model group (n=30) were fed with H10060 high-fat diet to induce obesity (DIO), blank control group (n=5) were fed with standard diet, both for 34 weeks. One day before the first administration, the model group was randomly divided into groups according to their body weight (average body weight range 45.0-52.0 g), with 5 mice in each group, which respectively were model control group, positive control group (semaglutide), and test sample group (1 #-4 # are compound 1, compound 4, compound 6 and compound 22, respectively). The blank control group and model control group were given saline subcutaneously every day, while the positive control group and test sample group were administrated by subcutaneous injection every day for 14 days. The body weight of the animals was weighed and recorded every day, and the change rate of body weight (%) was calculated by comparing the body weight at the last administration day with the initial body weight. The results are shown in Table 3 and FIG. 1.

Calculation formula: (initial body weight−last body weight)/initial body weight=body weight change rate (%).

Calculated positive values indicate a decrease and negative values indicate an increase.

TABLE 3

Effects of compounds on the body weight of DIO mice after 14 days' administration (%)

| Blank control group | Model control group | Positive control group | 1# | 2# | 3# | 4# |
|---|---|---|---|---|---|---|
| 2.51 | 2.13 | 13.20 | 28.3 | 22.0 | 22.0 | 26.0 |

2) Blood Glucose Lowering Effects on Glucose-Loaded Animal Model:

DIO mice fasted for 16 h, and 1 h after administration by subcutaneous injection, glucose solution (1 g/kg) was given intraperitoneally for glucose tolerance test. Blood glucose values were measured at 0.5, 1 and 1.5 h after glucose administration. The area under the blood glucose concentration curve (AUC) was calculated and compared with that of the model control group, and the blood glucose inhibition rate (%) was calculated. The results are illustrated in Table 4.

TABLE 4

Effects of compounds on the level of blood glucose under glucose load in DIO mice

| | Blank | Model | 1# | 2# | 3# | 4# | Positive group |
|---|---|---|---|---|---|---|---|
| AUC (mmol/) L · h | 6.94 ± 0.77 | 21.19 ± 0.92 | 7.24 ± 1.33** | 8.06 ± 2.06** | 8.66 ± 2.14** | 9.02 ± 1.74** | 8.97 ± 1.27** |
| AUC reduction rate (%) | | | 65.8** | 61.9** | 59.1** | 57.4** | 57.7** |

**compared with model control group, $P < 0.01$;
* compared with model control group, $P < 0.05$ Conclusion: as shown in Tables 3 and 4, the positive drug and the test compounds of the present invention showed a significant weight reduction effect and significantly improved glucose tolerance compared to the model group. The test compounds of the present invention have a blood glucose lowering effect comparable to that of the positive control drug, and can reduce body weight more significantly than the GLP-1 monoreceptor agonist (positive control drug).

Example 4

Effects of Compounds 27, 35, 54, 57 and 66 of Example 1 on Body Weight and Blood Glucose in Dio Mice Methods are the same as that in Example 3, the test results of effects on body weight are shown in Table 5, and the effects on blood glucose are shown in Table 6. In the table, 5 #-9 # are compound 27, compound 35, compound 54, compound 57, and compound 66, respectively.

TABLE 5

Effects of compounds on the body weight of DIO mice after 14 days' administration

| Blank control group | Model control group | Positive control group | 5# | 6# | 7# | 8# | 9# |
|---|---|---|---|---|---|---|---|
| −1.43 | 9.52 | 16.29 | 27.74 | 28.32 | 21.45 | 24.1 | 19.9 |

TABLE 6

| | Blank | Model | 5# | 6# | 7# | 8# | 9# | Positive |
|---|---|---|---|---|---|---|---|---|
| Effects of compounds on the level of blood glucose under glucose load in DIO mice | | | | | | | | |
| AUC (mmol/) L · h | 6.79 ± 1.06 | 19.88 ± 0.94 | 7.12 ± 1.30** | 8.99 ± 1.46** | 7.26 ± 1.77** | 8.11 ± 1.92** | 8.71 ± 2.10** | 8.33 ± 1.09** |
| AUC reduction rate (%) | | | 64.2** | 54.7** | 63.4** | 59.2** | 56.2** | 58.1** |

**compared with model control group, P < 0.01;
*compared with model control group, P < 0.05

Conclusion: as shown in Tables 5 and 6, compound 27, compound 35, compound 54, compound 57 and compound 66 significantly improved glucose tolerance (P<0.01) and significantly reduced body weight compared to untreated model control group. All the test compound administration groups showed a blood glucose lowering activity which is comparable to that of the positive drug, and had a more significant effect on weight loss compared with the positive drug.

Example 5

Effects of Short-Term Administration of the Compounds of Example 1 on Food Intake and Body Weight in Animal Model Method: diet-induced obese mice (DIO) with an average body weight of 52.5 g were divided into model control and test groups, 5 mice in each group. The test samples were dissolved in 10 mM PBS of pH7.4, injected once every 24 h at a dose of 30 nmol/kg, and administered twice. The model group was injected with solvent. Changes in food intake and body weight at 48 hours were measured, and the change rates were calculated compared to the day before administration. The results are illustrated in Table 7.

TABLE 7

Effects of short-term administration of test compounds on food intake and body weight in DIO mice

| Groups | Rate of change in food intake (%) | Body weight change (g) |
|---|---|---|
| Model group | +5 | −0.3 |
| Compound 1 | −58 | −2.8 |
| Compound 4 | −42 | −1.5 |
| Compound 13 | −67 | −2.3 |
| Compound 22 | −62 | −2.6 |
| Compound 27 | −55 | −1.9 |
| Compound 28 | −49 | −1.3 |
| Compound 35 | −59 | −3.2 |
| Compound 36 | −46 | −1.7 |
| Compound 54 | −35 | −0.9 |
| Compound 57 | −71 | −2.6 |
| Compound 66 | −56 | −1.7 |
| Compound 75 | −60 | −2.4 |
| Compound 77 | −51 | −2.9 |

Note:
+increase;
−decrease or reduce

The results in Table 7 show a significant decrease in food intake and a significant loss in body weight during administration of the test compounds compared to the model group, indicating that the weight-lowering effect of the test compounds is partially related to a decrease in food intake.

Example 6

Investigation of the Solubility of the Compounds of Example 1

2 mg of the compound was weighed, dissolved in 1 ml of phosphate buffer solutions with different concentrations (10, 20 mM) and different pH values (7.5, 8.0), and centrifuged, and supernatant was taken. The peak area was measured by HPLC (chromatographic column: Aeris widepore XB-C18 3.6 mm, 4.6×150 mm; mobile phase: A: 0.05% TFA, B: 95% acetonitrile; detection wavelength: 214 nm) and compared with a corresponding sample standard solution, and the relative concentration of the test sample solution is calculated. The results are illustrated in Table 8.

TABLE 8

Solubility of the compounds of Example 1 in phosphate buffer

| | Concentration | | | |
|---|---|---|---|---|
| | pH 7.5(mg/ml) | | pH 8.0(mg/ml) | |
| Sample | 10 mM | 20 mM | 10 mM | 20 mM |
| Glucagon | Insoluble | Insoluble | Insoluble | Insoluble |
| Compound 1 | >2 | >2 | — | — |
| Compound 2 | >2 | >2 | — | — |
| Compound 3 | 0.06 | Insoluble | 0.17 | 0.09 |
| Compound 4 | 1.82 | 1.22 | >2 | >2 |
| Compound 6 | 1.39 | 0.98 | >2 | 1.62 |
| Compound 9 | 1.50 | 1.07 | >2 | 1.76 |
| Compound 13 | >2 | >2 | — | — |
| Compound 16 | 0.14 | 0.05 | 0.16 | 0.20 |
| Compound 21 | >2 | >2 | — | — |
| Compound 22 | >2 | >2 | — | — |
| Compound 24 | >2 | >2 | — | — |
| Compound 25 | 0.3 | 0.1 | 0.5 | 0.2 |
| Compound 26 | 0.08 | Insoluble | 0.2 | 0.1 |
| Compound 27 | >2 | >2 | — | — |
| Compound 35 | 1.84 | 1.17 | >2 | >2 |
| Compound 42 | 1.72 | 1.51 | >2 | >2 |
| Compound 54 | 1.26 | 1.08 | 1.92 | 1.18 |
| Compound 57 | 1.46 | 1.31 | 1.84 | 1.53 |
| Compound 62 | 1.17 | 0.85 | 1.63 | 1.59 |
| Compound 66 | 1.49 | 1.42 | >2 | 1.88 |
| Compound 69 | >2 | >2 | — | — |
| Compound 75 | >2 | >2 | — | — |

Note:
—: undetected

Conclusion: as shown in Table 8, the solubility of the compounds of the present invention under physiologically acceptable pH conditions is improved as compared to glucagon, wherein the preferred embodiments of the present invention, i.e. the extended peptide derivatives of the shortened sequence of GC (1-26), have substantially increased solubility as compared to the conservative prosequence mutant extended peptide protocol (compound 3, compound 16, compound 25 and compound 26). Even in the case of modification by long-chain fatty acyl, the water solubility of the compounds under the acceptable condition of physiological pH is improved, which is beneficial to the preparation of pharmaceutical preparations.

Example 7

Chemical Stability of the Compounds of Example 1

The chemical stability of the compounds of the present invention in injection solution systems was evaluated by an accelerated stability test.

Methods: an appropriate amount of compound of Example 1 was weighed, and dissolved in 10 mM pH8.5 sodium hydrogen phosphate buffer. The final pH value of the solution was adjusted to 7.3 with 0.1 N hydrochloric acid, and proper amounts of Tween 80 and phenol were added. The mixture was placed at 10° C. and 37° C. for 14 days, and detected by HPLC-UV. The main peak area was obtained by peak area normalization method, and the changes compared with day 0 were investigated. The results are illustrated in Table 9.

The HPLC detection method was the same as that in Example 6, and the mobile phase gradient was appropriately adjusted according to the situation of chromatographic peak separation.

TABLE 9

Purity change of the compounds placed at 10° C. and 37° C. for 14 days in the injection solvent system

| Compound | Change in purity % (10° C.) | Change in purity % (37° C.) |
| --- | --- | --- |
| 1 | −1.4 | −5.2 |
| 4 | −0.9 | −3.7 |
| 13 | −2.8 | −6.9 |
| 22 | −2.0 | −5.7 |
| 27 | −1.8 | −4.6 |
| 35 | −0.6 | −3.1 |
| 57 | −1.1 | −4.0 |
| 66 | −2.7 | −5.1 |
| 75 | −1.9 | −4.5 |

Conclusion: the results in Table 9 show that the chemical stability of the test compounds in the preliminary injection formulation system is within the pharmaceutically acceptable range and has the potential to be optimally implemented.

The invention claimed is:

1. A polypeptide derivative, modified derivative or salt thereof, comprising a polypeptide having a sequence of general formula Ia:

$$HX^2QGTFTSDX^{10}SKYLEX^{16}X^{17}X^{18}$$
$$AX^{20}EFX^{23}X^{24}WLX^{27}X^{28}X^{29}X^{30}$$
(SEQ ID NO: 38)
General Formula Ia wherein,
$X^2$ is Ser or Aib;
$X^{10}$ is Tyr or Lys;
$X^{16}$ is Ser or Glu;
$X^{17}$ is Arg, Glu or Lys;
$X^{18}$ is Lys, Ala or Arg;
$X^{20}$ is Arg or Lys;
$X^{23}$ is Val or Ile;
$X^{24}$ is Ala, Glu or Lys;
$X^{27}$ is Leu or absent;
$X^{28}$ is Glu or absent;
$X^{29}$ is Ala;
$X^{30}$ is Z, and Z is a fragment peptide GGPSSG (SEQ ID NO:37);
one of $X^{10}$, $X^{17}$, $X^{20}$ or $X^{24}$ is Lys with a modified side chain; and
C-terminal carboxyl group is free or amidated.

2. The polypeptide derivative, modified derivative or salt thereof of claim 1, wherein the general formula Ia comprises:
$X^2$ is Aib;
$X^{16}$ is Glu;
$X^{17}$ is Arg or Lys;
$X^{20}$ is Lys;
$X^{27}$ is absent;
$X^{28}$ is Glu;
$X^{30}$ is Z; and
one of $X^{10}$ or $X^{20}$ is Lys with a modified side chain.

3. The polypeptide derivative, modified derivative or salt thereof of claim 1, wherein the general formula Ia comprises:
$X^{17}$ is Arg and $X^{18}$ is Ala;
$X^{17}$ is Arg and $X^{18}$ is Lys; or
$X^{17}$ is Lys and $X^{18}$ is Arg.

4. The polypeptide derivative, modified derivative or salt thereof of claim 1, wherein the general formula Ia comprises:
$X^{23}$ is Val and $X^{24}$ is Ala or Glu; or
$X^{23}$ is Ile and $X^{24}$ is Ala or Glu.

5. The polypeptide derivative, modified derivative or salt thereof, comprising a polypeptide having a sequence of general formula I:

$$HX^2QGTFTSDX^{10}SX^{12}YLX^{15}X^{16}X^{17}X^{18}$$
$$AX^{20}EFX^{23}X^{24}WLX^{27}X^{28}X^{29}X^{30}X^{31}$$
(SEQ ID NO: 36)
General Formula I wherein:
$X^2$ is Aib;
$X^{10}$ is Lys or Tyr;
$X^{12}$ is Lys or Arg;
$X^{15}$ is Asp or Glu;
$X^{16}$ is Glu;
$X^{17}$ is Arg or Lys;
$X^{18}$ is Lys, Ala or Arg;
$X^{20}$ is Arg or Lys;
$X^{23}$ is Val or Ile;
$X^{24}$ is Ala, Glu or Lys;
$X^{27}$ is absent;
$X^{28}$ is absent;
$X^{29}$ is Glu;
$X^{30}$ is Z;
$X^{31}$ is absent
Z is fragment peptide GGPSSG (SEQ ID NO:37);
C-terminal carboxyl group is free or amidated; and
wherein, one of $X^{10}$ or $X^{20}$ is Lys with a modified side chain.

6. The polypeptide derivative, modified derivative or salt thereof of claim 5, wherein the general formula I comprises:
$X^{17}$ is Arg and $X^{18}$ is Ala;
$X^{17}$ is Arg and $X^{18}$ is Lys; or
$X^{17}$ is Lys and $X^{18}$ is Arg.

7. The polypeptide derivative, modified derivative or salt thereof of claim 5, wherein the general formula I comprises:
$X^{23}$ is Val and $X^{24}$ is Ala or Glu; or
$X^{23}$ is Ile and $X^{24}$ is Ala or Glu.

8. The polypeptide derivative, modified derivative or salt thereof of claim 1, wherein $X^{10}$ is Tyr and $X^{20}$ is Lys with a modified side chain.

9. The polypeptide derivative, modified derivative or salt thereof of claim 8, wherein the Lys side chain is modified by coupling a fatty acid to a hydrophilic linker fragment at ε-amino group.

10. The polypeptide derivative, modified derivative or salt thereof of claim 9, wherein the hydrophilic linker fragment is selected from a fragment consisting of one or more of Glu, γGlu, Gly and Ado (8-amino-3,6-dioxyoctanoic acid).

11. The polypeptide derivative, modified derivative or salt thereof of claim 9 wherein the fatty acid is a $C_{14\text{-}20}$ fatty acid.

12. A pharmaceutical composition comprising the polypeptide derivative, modified derivative or salt thereof of claim 1.

13. A method for treating a metabolic disease, comprising administering to a patient in need thereof the polypeptide derivative, modified derivative or salt thereof of claim 1.

14. The polypeptide derivative, modified derivative or salt thereof of claim 10, wherein the hydrophilic linker fragment is γGlu-γGlu-, Glu-γGlu-, Glu-γGlu-, γGlu-Gly-Gly, γGlu-Gly-γGlu-, γGlu-Ado-Ado-; Ado-Ado-γGlu- or γGlu-Ado-Ado-γGlu-.

15. The polypeptide derivative, modified derivative or salt thereof of claim 9, wherein the fatty acid is a $C_{16\text{-}20}$ fatty diacid.

16. The method of claim 13, wherein the metabolic disease is diabetes, obesity, fatty liver disease, hyperlipidemia and/or metabolic syndrome.

17. The method of claim 16, wherein the fatty liver disease is non-alcoholic fatty liver disease.

18. A pharmaceutical composition comprising the polypeptide derivative, modified derivative or salt thereof of claim 1 and a pharmaceutically acceptable excipient.

19. A pharmaceutical composition comprising the polypeptide derivative, modified derivative or salt thereof of claim 5 and a pharmaceutically acceptable excipient.

20. A method for treating a metabolic disease, comprising administering to a patient in need thereof the polypeptide derivative, modified derivative or salt thereof of claim 5.

* * * * *